United States Patent [19]
Horn

[11] Patent Number: 5,523,214
[45] Date of Patent: Jun. 4, 1996

[54] METHOD OF VISUALLY DEMONSTRATING THE PRESENCE OF MICROORGANISMS, IDENTIFYING THEM, AND TESTING THEM FOR SENSITIVITY TO ANTIBIOTICS WITH REDOX INDICATORS

[75] Inventor: Jurgen Horn, Egelsbach, Germany

[73] Assignee: Biotest Aktiengesellschaft, Dreieich, Germany

[21] Appl. No.: 239,808

[22] Filed: May 9, 1994

[30] Foreign Application Priority Data

May 17, 1993 [DE] Germany ................ 43 16 394.7

[51] Int. Cl.⁶ ................ C12Q 1/18; C12Q 1/02
[52] U.S. Cl. ................ 435/52; 435/29; 435/4; 435/863; 435/864; 435/865; 435/866
[58] Field of Search ................ 435/29, 32, 4, 435/863, 864, 865, 866

[56] References Cited

U.S. PATENT DOCUMENTS 5,126,247  6/1992  Palmer et al. ................ 435/25
5,316,918  5/1994  Ollar ................ 435/34

FOREIGN PATENT DOCUMENTS 9008196  7/1990  WIPO.

OTHER PUBLICATIONS

C. Ramsdell et al., J. Dairy Sci., vol. XVIII, No. 11, pp. 705–717, 1935.
Mundinger et al., Molkerei Zeitung, vol. 47(9), pp. 171–174, 1933.
The Merch Index, Eleventh Edition, 1989, pp. 954, 894, 1433.

Primary Examiner—Chhaya D. Sayala
Attorney, Agent, or Firm—Sprung Horn Kramer & Woods

[57] ABSTRACT

A method of visually demonstrating the growth of such microorganisms as fungi, yeasts, and bacteria, especially mycobacteria, identifying them, and testing them for sensitivity to antibiotics by the color change of a specific redox indicator system. A mixture of the redox indicators Methylene Blue and resazurin is added to the culture medium. Iron(III) salts mixed with $K_3Fe(CN)_6$, Iron(II) salts mixed with $K_4Fe(CN)_6$, or sodium tungstate $(Na_2WO_4)$ is added to the culture medium.

8 Claims, No Drawings

METHOD OF VISUALLY DEMONSTRATING THE PRESENCE OF MICROORGANISMS, IDENTIFYING THEM, AND TESTING THEM FOR SENSITIVITY TO ANTIBIOTICS WITH REDOX INDICATORS

The present invention concerns a method of visually demonstrating the growth of such microorganisms as fungi, yeasts, and bacteria, especially mycobacteria, identifying them, and testing them for sensitivity to antibiotics by observing changes in color in a specific redox indicator system comprising methylene blue and resazurin or salts of iron(III) or iron(II) salts combined with $K_3Fe(CN)_6$ or $K_4Fe(CN)_6$ or sodium tungstate ($Na_2WIPO_4$).

Microorganisms obtained from various specimens (urine, matter from wounds and abscesses, blood, and sputum) are isolated as primary cultures. Growth is visible in the form of colonies of bacteria on the agar dishes employed for primary isolation.

Gels or broths with various substrates are employed for identification. The growth of bacteria is indicated by turbidity or color changes. Many different color changes, called color streaks (DIN 58 959, 9, Supplement 1), occur, depending on the particular substrate employed.

Also known is a uniform color change obtained from 95 different substrates with the redox indicator tetrazolium violet to demonstrate the bacteria's metabolic activity (Bochner, American Clinical Laboratory, p. 14, April 1991).

Sensitivity is tested by agar diffusion or broth dilution, microdilution for instance (DIN 58 940, Parts 1, 2, & 8). The results are determined by the turbidity of the broth or the propagation of colonies on the gel. Also known is the use of the redox indicator resazurin for visually demonstrating bacterial growth when testing for sensitivity by color change (WIPO 90/08196). Since the indicator's color depends on its pH, an alkaline buffer is preferred. A redox stabilizer (potassium hexacyanoferrate) is needed to prevent the substrate itself from inducing a color change without bacterial growth.

EP B 0 135 023 discloses detecting intracellular oxidoreductase with redox indicators for testing the sensitivity of exclusively bactericidal antibiotics that act primarily on murein biosynthesis. Only the enzymes released by the dying cells are detected, and not growth (in terms of the metabolism of the growing cells).

The Journal of Dairy Sciences (1935, p. 705), says that resazurin employed as a redox indicator for detecting bacterial contamination in milk turns color substantially more rapidly than methylene blue (cf. also Sigma-Aldrich Handbook of Stains and Dyes, p. 622). This action is obviously related to resazurin's change from blue to red. Methylene blue only changes from blue to colorless.

The method described in EP B 0 130 023 is as mentioned hereintofore possible only with antibiotics, penicillin for instance, that have a bactericidal action on murein biosynthesis. It fails on the other hand with such other bacteriostatics as tetracycline, and its practicality is restricted. The method described in WIPO 90/08196 can on the other hand be employed to test for sensitivity to various antibiotics over 15 to 24 hours. The method of generally demonstrating the growth and of testing the sensitivity of mycobacteria cannot on the other hand be employed with the method described in WIPO 90/08196 because tests have indicated that the combination of the redox indicator resazurin and the redoxy stabilizer potassium hexacyanoferrate alone change the sterile medium from blue to red subsequent to 48 to 72 hours in the incubator. This phenomenon simulates growth that does not actually exist. The reason is the long incubation required by mycobacteria.

The rapidly growing mycobacteria require approximately a week to demonstrate growth, whereas such slow-growing tuberculosis agents as M. tuberculosis and M. bovis and the M. avium that appears in AIDS patients require at least 8 to 10 weeks of incubation (DIN 58943, Part 3).

Incubation for 4 weeks is necessary (DIN 58943, Part 8) to test the sensitivity of mycobacteria raised on solid substrates, whereas only 1 week is required for fluid nutrients.

The object of the present invention is accordingly a method of visually demonstrating the growth of microorganisms, identifying them, and testing them for sensitivity to various active ingredients that is not restricted to specific antibiotics, whereby the environment will be stable enough to detect even such organisms with longer incubation times as mycobacteria without false positive results.

This object is attained in accordance with the present invention as will now be described. A mixture of the indicators methylene blue and resazurin is added to the substrate or environment. Not enough of the mixture is added to be toxic to the microorganisms. The ratio of the mixture is 1:4 to 1:80. The mixture consists of 1 to 200 mg and especially 1 to 20 mg of methylene blue and of 5 to 100 mg and especially 7.5 to 50 mg of resazurin per liter of substrate. The substrate is iron(III) salts mixed with $K_3Fe(CN)_6$, iron(II) salts mixed with $K_4Fe(CN)_6$, or sodium tungstate ($Na_2WIPO_4$).

It has been discovered that a mixture of the indicators methylene blue and resazurin surprisingly demonstrates the growth of bacteria by changing color from blue to red considerably more rapidly than resazurin alone will. The color changes in response to enterobacteria in 2 to 3 hours and in 5 to 7 hours in response to nonfermenters for example (cf. Tables 1–5). Another surprise is that the sterile medium by itself will remain a stable blue for 4 weeks or longer. Such phenomena could not have been predicted from the aforesaid publications, especially the Journal of Dairy Science. From that article it would be expected that a mixture of a methylene blue and resazurin would take substantially longer to change from blue to red. Resazurin does so rapidly of course, but methylene blue changes much more slowly and from blue to colorless. The expected result would be an original violet that would only turn red once the methylene blue had faded. In the presence of the redox stabilizer potassium hexacyanoferrate (which is intended to prevent the uncontaminated substrate from turning prematurely and does so as described in WIPO 90/08196 for 48 to 72 hours) the change when induced by bacterial growth should accordingly take definitely longer. In accordance with the present invention, however, the transformation is rapid.

The effect can be improved by adding such a redox stabilizer as potassium hexacyanoferrate, $K_4Fe(CN)_6$. The sterile substrate will remain a stable blue for 2 to 3 months at 35° to 37° C. The growth of enterobacteria will be demonstrable in 3 to 4 hours. The growth and sensitivity of such microorganisms as enterobacteriacene for example can be rapidly detected. The growth and sensitivity to antibiotics of such slow-growing organisms as mycobacteria on the other hand have hitherto been demonstrable on solid substrates by waiting for colonies to form or in broths by incorporating the radioactive isotope C14. These properties as well will now be rapidly apparent.

Particularly appropriate redox stabilizers are $K_3Fe(CN)_6$, Tartrazine Yellow, Reactive Red 4, (2,7-Napthalene-disulfonic acid, 5-(benzoylamine)-3-[[5-[[4-chloro-6-[(4-sulfophenyl)amino]-1, 3, 5-triazin-2-yl]amino]-2-sulfophenyl]azo]-4-hydroxy-, tetrasodium salt) $NH_4Fe(SO_4)_2$, Malachite Green, and combinations thereof with the hereintofore discussed $K_4Fe(CN)_6$. Portions of 0.01–20%, particularly 0.01–10%, and very particularly 1–2.5% of the stabilizers are added per liter of nutrient.

Another surprising discovery is that mixtures of such inorganic salts of iron(III) as $NH_4Fe(SO_4)_2$ and $K_3Fe(CN)_6$ or iron(II) and $K_4Fe(CN)_6$ on the one hand or $Na_2WO_4$ alone on the other can be employed in culture media as redox indicators to demonstrate the growth of microorganisms, identify them, or test their sensitivity. This is because a color change from yellowish brown to blue by way of bluish green will occur in the absence of metabolism-selective organisms due to the redox processes Berlin Blue, Turnbull's Blue, or Tungsten Blue triggered by the microorganisms.

This combination of redox indicators results like the combination of methylene blue and resazurin in culture media stable enough to be reliably employed even after being stored for some time to detect microorganisms, even those like mycobacteria that take long to incubate, to identify them, and to test their sensitivity to antibiotics. This property could not have been predicted because indicator systems that contain iron or $Na_2WO_4$ have been employed until now only to detect bacteria that produce $H_2S$. That they could be utilized to detect aerobic organisms as well was accordingly surprising.

Like the combination of methylene blue and resazurin, the aforesaid stabilizers can be added to the culture medium along with an indicator system containing iron or $Na_2WO_4$. The mixture will remain stable for weeks without losing its activity.

Especially preferred iron-containing systems are combinations of $NH_4Fe(SO_4)_2$ and $K_3Fe(CN)_6$ and of $NH_4FeSO_4$ and $K_4Fe(CN)_6$. Portions of 1–10% and preferably of 0.1–10% of these or of $Na_2WO_4$ are added per liter of nutrient. The preferred ratios range from 1:4 to 1:10 of salt of iron(III) or iron(II) to $K_3$ or $K_4Fe(CN)_6$.

The method in accordance with the present invention can be employed to detect various microorganisms. Among them are yeasts, fungi, nonfermenters, cocci, bacilli, coccobacilli, and enterobacteria and preferably the aforesaid mycobacteria *M. tuberculosis, M. avium,* and *M. bovis.* Their sensitivities to such various agents as erythromycin, tetracycline, penicillin, oflatoxin, oxacillin, cefotoxin, etc. and especially to such tuberculostatics as isoniazid, dihydrostreptomycin, and ethambutol can be tested simultaneously.

Microorganism growth is demonstrated in the method in accordance with the present invention in test tubes containing approximately 3 to 4 ml of medium. Standard microtitration plates that accommodate 100 µl in each depression can alternatively be employed. Such plates are also appropriate for sensitivity testing and for reactions identifying the microorganism. Such conventional culture mediums as Müller-Hinton medium can be employed in normal incubation conditions or any variation known to one of skill in the art. Such conventional buffers and nutrients as phosphate and carbonate can be employed with the pH neutral or in the acidic range between 6.4 and 8.

The present invention will now be specified with reference to examples.

I.

Examples 1–3. Sensitivity of Normally Growing Bacteria to Antibiotics 1. 22.0 g of Müller-Hinton medium are dissolved in 1 l of 0.1 molar phosphate buffer with a pH of 7.4 and autoclaved. 0.005 g of resazurin and 422 mg of $K_4Fe(CN)_6$, 0.001 molar, are added and dissolved.

The resulting solution is employed as is as a sterile reference and to dissolve various antibiotics for sensitivity testing.

2. 22.0 g of Müller-Hinton medium are dissolved in 1 l of 0.1 molar phosphate buffer with a pH of 7.2 and autoclaved. 0.005 g of resazurin, 0.00125 g of methylene blue, and 422 mg of $K_4Fe(CN)_6$ are added and dissolved.

The resulting solution is employed as is as a sterile reference and to dissolve various non-β-lactam antibiotics for sensitivity testing.

3. 22.0 g of Müller-Hinton medium are dissolved in 1 l of 0.1 molar phosphate buffer with a pH of 6.8 and autoclaved. 0.005 g of resazurin, 0.00125 g of methylene blue, and 422 mg of $K_4Fe(CN)_6$ are added and dissolved.

The resulting solution is employed as is as a sterile reference and to dissolve various β-lactam antibiotics for sensitivity testing.

The media prepared as described in Examples 1 through 3 are tested with the bacterial stains *S. aureus* ATCC 29213, *E. coli* ATCC 25922, and *P. aeruginosa* ATCC 27853 against erythromycin, tetracycline, ofloxacin, cefotoxin, and penicillin G. The results are summarized in Table 1. Example 1 represents the comparison disclosed in WIPO 90/08196 and Examples 2 and 3 the one in accordance with the present invention.

TABLE 1

|  | Ex. 1 (Ref.) | | | | | | | Ex. 2 (Inv.) | | | | | | |
| --- | --- | --- | --- | --- | --- | --- | --- | --- | --- | --- | --- | --- | --- | --- |
|  | 3 h | 5 h | 7 h | 10 h | 24 h | 48 h | 72 h | 3 h | 5 h | 7 h | 10 h | 24 h | 48 h | 72 h |
| Reference | . | . | . | . | . | +/- | + | . | . | . | . | . | . | . |
| *S. aureus* ATCC 29213 | | | | | | | | | | | | | | |
| Erythromycin | . | + | + | + | + | + | + | + | + | + | + | + | + | + |
| Tetracyclin | . | + | + | + | + | + | + | + | + | + | + | + | + | + |
| Ofloxacin | . | + | + | + | + | + | + | + | + | + | + | + | + | + |
| Oxacillin | . | + | + | + | + | + | + | nd | | | | | | |
| Cefotaxim | . | + | + | + | + | + | + | nd | | | | | | |
| Penicillin G | . | + | + |  | + | + | + | nd | | | | | | |
| *E. coli* ATCC 25922 | | | | | | | | | | | | | | |
| Erythromycin | kW | kW | kW | kW | kW | kW | kW | kW | kW | kW | kW | kW | kW | kW |
| Tetracyclin | . | + | + | + | + | + | + | + | + | + | + | + | + | + |
| Ofloxacin | . | + | + | + | + | + | + | + | + | + | + | + | + | + |

TABLE 1-continued

| | | | | | | | | | | | | | | |
|---|---|---|---|---|---|---|---|---|---|---|---|---|---|---|
| Oxacillin | kW | kW | kW | kW | kW | kW | kW | nd | | | | | | |
| Cefotaxim | · | kW | kW | kW | kW | kW | kW | nd | | | | | | |
| Penicillin G | kW | kW | kW | kW | kW | kW | kW | nd | | | | | | |
| P. aeruginosa ATCC 27853 | kW | kW | kW | kW | kW | kW | kW | kW | kW | kW | kW | kW | kW | kW |
| Erythromycin | | | | | | | | | | | | | | |
| Tetracyclin | · | · | · | + | + | + | + | · | +/- | + | + | + | + | + |
| Ofloxacin | · | · | · | + | + | + | + | · | +/- | + | + | + | + | + |
| Oxacillin | kW | kW | kW | kW | kW | kW | kW | nd | | | | | | |
| Cefotaxim | · | · | · | + | + | + | + | nd | | | | | | |
| Penicillin G | kW | kW | kW | kW | kW | kW | kW | nd | | | | | | |

| | | Ex. 3 (Inv.) | | | | | | |
|---|---|---|---|---|---|---|---|---|
| Reference | | · | · | · | · | · | · | · |
| S. aureus ATCC 29213 | | | | | | | | |
| Erythromycin | nd | | | | | | | |
| Tetracyclin | nd | | | | | | | |
| Ofloxacin | nd | | | | | | | |
| Oxacillin | + | + | + | + | + | + | + | |
| Cefotaxim | + | + | + | + | + | + | + | |
| Penicillin G | + | + | + | + | + | + | + | |
| E. coli ATCC 25922 | | | | | | | | |
| Erythromycin | nd | | | | | | | |
| Tetracyclin | nd | | | | | | | |
| Ofloxacin | nd | | | | | | | |
| Oxacillin | kW | kW | kW | kW | kW | kW | kW | |
| Cefotaxim | + | + | + | + | + | + | + | |
| Penicillin G | kW | kW | kW | kW | kW | kW | kW | |
| P. aeruginosa ATCC 27853 | nd | | | | | | | |
| Erythromycin | | | | | | | | |
| Tetracyclin | nd | | | | | | | |
| Ofloxacin | nd | | | | | | | |
| Oxacillin | kW | kW | kW | kW | kW | kW | kW | |
| Cefotaxim | · | +/- | + | + | + | + | + | |
| Penicillin G | kW | kW | kW | kW | kW | kW | kW | | nd: not done (Ex. 2 only for non-B-lactam antibiotics, Ex. 3 for B-lactam antiobiotics
·: minimal-inhibition concentration prescribed by NCCLS not readable
+: minimal-inhibition concentration prescribed by NCCLS already readable
kw: NCCLS provides no prescription
For sterile references:
·: sterile
+: color change means growth, unstable. Since no growth could be demonstrated, Example 1 is a false positive finding. Examples 2 and 3 provide time-independent findings.

| | NCCLS (National Committee for Clinical Laboratory Standards) levels Antibiotic: Erythromycin Tetracycline Ofloxacin Oxacillin Cefotoxin Penicillin C | | | | | |
|---|---|---|---|---|---|---|
| Antibiotic Germ | Erythromycin | Tetrazyklin | Ofloxacin | Oxacillin | Cefotaxim | Penicillin G |
| S. aureus ATCC 29213 | 0.12–0.5 µg/ml | 0.25–1 | 0.12–1 | 0.12–0.5 | 1–4 | 0.25–1 |
| E. coli ATCC 25922 | — | 1–4 | 0.015–0.12 | — | 0.06–0.25 | — |
| P. aeruginosa ATCC 27853 | — | 8–32 | 1–8 | — | 4–16 | — |

Table 1 indicates that the media with methylene blue and resazurin (Ex. 2 & 3) provide more rapid recognition of the antibiogram. It will also be evident that the sterile reference remains specifically negative longer (blue) and changes color not unspecifically (still red). This makes it possible to postpone evaluating a batch for several days (over the weekend, for example, where there is no one in the laboratory).

II.

DEMONSTRATING GROWTH OF SLOWLY GROWING BACTERIA

Example 4. Preparing the Culture Medium 11.0 g of Müller-Hinton medium are dissolved in 1 l of 0.1 molar phosphate buffer at a pH of 6.8 for β-lactam antibiotics or in 1 l of 0.1 molar phosphate buffer at a pH of 7.2 for non-β-lactam antibiotics and autoclaved. 0.02 g of resazurin, 0.005 g of methylene blue, 10 mg of Reactive Red 4, and 422 mg of $K_4Fe(CN)_6$ are added and dissolved. The resulting solution is employed as is as a sterile reference or to dissolve various antibiotics for sensitivity testing. This composition provides better correlation with the NCCLS method in evaluating clinical isolates and a wider range of antibiotics than with the restricted selection of germs tested as described in Examples 1 through 3.

Example 5a, b, c, d, e, f, g. Preparing a Broth for Detecting Mycobacteria

A mixture is prepared from the constituents
Difco Middlebrook 7H9 broth, 4.7 g $KH_2PO_4$, 3.5 g $Na_2KPO_4$, 2.5 g L-Asparagine, 0.1 g Potassium aspartate, 3.0 g Sodium pyruvate, 0.5 g Haemin (already dissolved in NaOH), 1.66 mg Glucose, 0.5 g Glycerol, 5 m Distilled water, 900 ml.

The pH is 6.40.

The substances are dissolved and autoclaved 15 minutes at 121° C. A mixture of calf's serum, 100 m catalase solution, 0.3 ml and ribonucleic acid (in ethanol), 25 mg is added to the medium. The result is a base medium with a final volume of 1 l and a pH of 6.40.

Modification e 40 mg of resazurin, 10 mg of methylene blue, and 2.54 g of $K_4Fe(CN)_6$ are added to 1 l of the base medium.

Modification f 40 mg of resazurin, 10 mg of methylene blue 2 54 g of $K_4Fe(CN)_6$, 1 mg of Malachite Green, and 20 mg of Tartrazine Yellow are added to 1 l of the base medium.

Modification g 20 mg of resazurin and 1.69 g of $K_4Fe(CN)_6$ are added to 1 l of the base medium.

The media prepared as described in Examples 5 a–g are tested for growing mycobacteria with Modification g (resazurin alone) as a reference in accordance with WIPO 90/08196. Table 2 summarizes the results.

TABLE 2

|  | M. avium | M. chelonae | M. fortuitum | M. peregrinum | E. coli ATCC 25922 |
|---|---|---|---|---|---|
| Mod. a, inoculated | 8–17 days | 4–9 days | 3–6 days | 4–9 days | 1 day* |
| Mod. a, sterile ref. | neg. blue 8 weeks later | | | | |
| Mod. b, inoculated | 8–17 days | 4–9 days | 4–7 days | 5–10 days | inhibited by Malachite Green |
| Mod. b, sterile ref. | neg. blue 10 weeks later | | | | |
| Mod. c, inoculated | 8–17 days | 4–9 days | 3–6 days | 4–9 days | 1 day |
| Mod. c, sterile ref. | neg. blue 10 weeks later | | | | |
| Mod. d, inoculated | 9–17 days | 4–9 days | 3–6 days | 4–9 days | 1 day |
| Mod. d, sterile ref. | neg. blue 10 weeks later | | | | |
| Mod, e. inoculated | 8–17 days | 4–9 days | 3–6 days | 5–10 days | 1 day |
| Mod. e, sterile ref. | neg. blue 10 weeks later | | | | |
| Mod. f, inoculated | 8–17 days | 5–10 days | 4–7 days | 5–10 days | inhibited by Malachite Green |
| Mod. f, sterile ref. | neg. blue 12 weeks later | | | | |
| Mod. g, inoculated | 8 days** | 7–8 days** | 7–8 days** | 7 days** | 1 day |
| Mod. g, sterile ref. | 8 days** | 8 days** | 8 days** | 7 days** | 7 days |

The time interval for the growth indicated by a color change to red depends on the various concentrations of germs. The most rapid change is attained with the highest tested germ concentration in the inoculum (Mcfarland $0.5 \cdot 10^{-3}$) and the slowest with the lowest germ concentration (Mcfarland $0.5 \cdot 10^{-7}$).
*Evaluated every day instead of every hour, so that 1 day is listed as the first evaluation time for E. coli. The color change occurs in a few hours, however.
**Since the uninoculated sterile reference changed color in 8 days, it is impossible to decide whether the change in the inoculated tubes is to be ascribed to growth or only to the non-specific color change of the medium.

Modification a 20 mg of resazurin, 5 mg of methylene blue, and 1.69 g of $K_4Fe(CN)_6$ are added to 1 l of the base medium.

Modification b 20 mg of resazurin, 5 mg of methylene blue, 1.69 g of $K_4Fe(CN)_6$, and 1 mg of Malachite Green are added to 1 l of the base medium.

Modification c 20 mg of resazurin, 5 mg of methylene blue, 1.69 g of $K_4Fe(CN)_6$, and 20 mg of Tartrazine Yellow are added to 1 l of the base medium.

Modification d 20 mg of resazurin, 5 mg of methylene blue, 1.69 g of $K_4Fe(CN)_6$, and 20 mg of Reactive Red 4 are added to 1 l of the base medium.

It will be evident from Table 2 that medium 5g (the reference), which contains only resazurin and $K_4Fe(CN)_6$, always turns red unspecifically and too rapidly to reveal whether the mycobacteria growing in the medium grow rapidly or slowly. Even rapidly growing mycobacteria do not grow rapidly enough for the color change to differentiate from the unspecific result due to incubation of the sterile medium.

In all other modifications of the present invention that involve methylene blue and resazurin (5a–5f), the uninoculated sterile reference is still negative (blue) after 8 to 12 weeks of incubation, allowing definite differentiation from the change to red deriving from growth. The same indication of growth is also very rapid and sensitive in the slowly growing Mycobacterium avium, which needs approximately 3 to 6 weeks on a solid substrate, occurring very readily in a very rapid 8 to 17 days.

III.

Testing Sensitivity in Slowly Growing Mycobacteria

Example 6

The culture medium described in Example 5A is employed, but without the catalase solution. The medium is employed both as is as a sterile reference and as a solute for the tuberculostats isoniazid, dehydrostreptomycin, and ethambutol. The isoniazid is tested at concentrations of 0.03, 0.06, 0,125, 0.25, 0.5, 1.0, 2.0 and 4.0 mg/l, the dehydrostreptomycin at concentrations of 0.5, 1.0, 2.0, 4.0, 8.0, 16.0, 32.0, and 64.0 mg/l, and the ethambutol at concentrations of 0.125, 0.25, 0.5, 1.0, 2.0, 4.0, 8.0 and 16.0 mg/l. 0.1 ml of each solution is loaded into microtitration plate and frozen. The samples are thawed and inoculated with bacterial suspensions of 1 mg/ml and with dilutions there of 10/2, 10/3 and 10/4. The same bacterial suspensions of M. tuberculosis strains are employed to inoculate conventional Löwenstein-Jensen media with the same concentrations of tuberculostats. The strains can be classified resistant or sensitive just as well with either the medium in accordance with the invention or with the Löwenstein-Jensen media, although the former is ready to interpret in a week while the conventional media require three to four weeks.

IV.

Identification Reactions

Example 7

A 100 millimolar phosphate buffer with a pH of 7.2 and containing 1 g/l of magnesium sulfate, 1 g/l of ammonium chloride, and 0.05 g/l of Tryptone (Difco) is employed to supply the bacteria with the basic nutrients they require. Proteose-Peptone or 0.04 g of Tryptone or Proteose-Peptone with 0.01 g of yeast extract can be employed instead of the 0.05 g of Tryptone. The buffer can alternatively be a carbonate buffer or morpholinpropane sulfonate or similar. Approximately 20 mM/l of the substrates to be catabolized are employed. The medium also contains a growth indicator in the form of 20 mg of resazurin, 5 mg of methylene blue, and 1.69 g of $K_4Fe(CN)_6$ per liter.

Table 3 lists the results.

TABLE 3

| Substrate Germ | Citrate | Lactose | Adontitol | Acetate |
|---|---|---|---|---|
| E. coli | − | + | − | + |
| C. freundii | + | + | − | + |
| C. diversus | + | + | + | + |

It will be evident from Table 3 that the indicator mixture in accordance with the present invention can also be employed to differentiate the germs down to the species level, which is to identify them.

V.

Indicator Mixtures Containing Iron or $Na_2WO_4$

Example 8

1.2 g of $K_3Fe(CN)_6$ and 4.8 g of $NH_4FE(III)(SO_4)_2 \times 12$ $H_2O$ are added to the medium described in Example 5.

The sterile medium retains its brownish-yellow color during incubation. The medium inoculated with E. coli ATCC 25 922 changes to blue as a result of the metabolism of the growing bacteria.

Example 9

2.94 g of $Na_2WO_4 \times 2$ $H_2O$ are added to the medium described in Example 5.

The sterile medium is still yellowish 48 hours after incubation and acidification with 12% sulfuric acid.

The medium inoculated with E. coli ATCC 25 922 turns blue 48 hours later when acidified as a result of the metabolism of the growing bacteria.

VI.

Stability Tests

Media in accordance with the present invention were compared in Examples 10 through 13 with the method with no redox stabilizer as described in WO 90/08196.

Example 10. WIPO 90/08196 Compared With Müller-Hinton medium 22.0 g of Müller-Hinton medium are dissolved in 1 liter of 0.1 molar phosphate buffer with a pH of 7.4 and autoclaved. 0.02 g of resazurin are added and dissolved. The resulting solution is employed as is as a sterile reference and to dissolve various antibiotics to test sensitivity.

Example 11. Present Invention Compared With Müller-Hinton Medium 22.0 g of Müller-Hinton medium are dissolved in 1 liter of 0.1 molar phosphate buffer with a pH of 7.4 and autoclaved. 0.02 g of resazurin and 0.005 g of methylene blue are added in accordance with the present invention and dissolved. The resulting solution is employed as is as a sterile reference and to dissolve various antibiotics to test sensitivity.

The results are summarized in Table 4.

TABLE 4

| | Ex. 10 | | | | | | | Ex. 11 | | | | | | |
|---|---|---|---|---|---|---|---|---|---|---|---|---|---|---|
| | 3 h | 5 h | 7 h | 10 h | 24 h | 48 h | 72 h | 3 h | 5 h | 7 h | 109 h | 20 h | 48 h | 72 h |
| Sterile Reference | − | − | − | − | +/− | + | + | − | − | − | − | − | − | − |
| S. aureus ATCC 2921 Tetracyclin | − | − | − | + | + | + | + | − | − | + | + | + | + | + |
| Ofloxacin | − | − | − | + | + | + | + | − | − | + | + | + | + | + |
| E. coli ATCC 25922 Tetracyclin | − | − | − | + | + | + | + | − | − | + | + | + | + | + |

TABLE 4-continued

|  | Ex. 10 | | | | | | | Ex. 11 | | | | | | |
| --- | --- | --- | --- | --- | --- | --- | --- | --- | --- | --- | --- | --- | --- | --- |
|  | 3 h | 5 h | 7 h | 10 h | 24 h | 48 h | 72 h | 3 h | 5 h | 7 h | 109 h | 20 h | 48 h | 72 h |
| Ofloxacin | − | − | − | + | + | + | + | − | − | + | + | + | + | + |

− = minimal inhibiting concentration still not readable
+ = minimal inhibiting concentration capable of interpretation
For the sterile reference:
− = sterile
+ = color change, indicating growth and lack of sterility although, since no growth was demonstrable, Example 10 is a false positive. Example 11 provides time-independent correct results.

The following will be evident from Table 4.

Example 11 (resazurin and Methylene Blue in accordance with the present invention) demonstrates in comparison with Example 10 (only resazurin, reference) that a stable product can be obtained with the combination in accordance with the invention with which no non-specific color change can occur even without redox stabilizers. This result is impossible with the known mixture without stabilizers.

Example 12. (Reference. Liquid Medium for Mycobacteria)

The medium from Example 5a (liquid medium for Mycobacteria) is employed. 20 mg of resazurin are added to 1 l of medium.

Example 13. (Invention. Liquid Medium for Mycobacteria Plus Resazurin)

The medium from Example 5a is employed. 20 mg of resazurin and 5 mg of Methylene Blue are added to 1 l of medium.

The results of this comparison are summarized in Table 5.

TABLE 5

|  | Example 12 | Example 13 |
| --- | --- | --- |
| Sterile Reference | Changed to red two days later, indicating growth | +/− (violet) 4 weeks later, changed to red 5 weeks later, indicating growth |
| M. avium | Changed to red 2 days later, indicating growth | took 8 to 17 days to change to red, indicating growth |
| M. chelonae | Changed to red 2 days later, indicating growth | took 4 to 9 days to change to red, indicating growth |

The time interval for the growth indicated by a color change to red depends on the various concentrations of germs. The most rapid change is attained with the highest tested germ concentration in the inoculum (Mcfarland $0.5 \cdot 10^{-3}$) and the slowest with the lowest germ concentration (Mcfarland $0.5 \cdot 10^{-7}$).

*Since the uninoculated sterile reference changed color in 2 days, it is impossible to decide whether the change in the inoculated tubes is to be ascribed to growth or only to the non-specific color change of the medium.

Table 5 demonstrates that the combination in accordance with the present invention (Example 12: resazurin and Methylene Blue) results in a relatively stable product that makes it possible to demonstrate the growth of rapidly and slowly growing Mycobacteria. The medium in accordance with the invention (no color change for 5 weeks, or 35 days) is in itself 17 times more stable than the known mixture with resazurin (Example 13), which changes color in even 2 days.

I claim:

1. A method of visually demonstrating the growth of fungi, yeasts or bacteria, identifying the species of said fungi, yeasts or bacteria and testing the sensitivity of said fungi, yeasts or bacteria to antibiotics in a culture medium wherein a mixture consisting of:

methylene blue and resazurin; and a redox stabilizer or mixture of stabilizers selected from the group consisting of Tartrazine Yellow, Reactive Red 4, Malachite Green, $NH_4Fe(SO_4)_2$, and $K_4Fe(CN)_6$ is added to the culture medium.

2. A method according to claim 1, wherein the bacteria is Mycobacteria.

3. A method according to claim 1, wherein the sensitivity of Mycobacteria to antituberculostatics is demonstrated.

4. A method according to claim 1, wherein Methylene Blue and resazurin are employed in a ratio ranging from 1:4 to 1:80.

5. A method according to claim 1, wherein the amount of Methylene Blue present in the mixture is 1–200 mg, per liter of medium.

6. A method according to claim 1, wherein the amount of Methylene Blue present in the mixture is 1–20 mg per liter of medium.

7. A method according to claim 1, wherein the amount of resazurin present in the mixture is 5–100 mg per liter of medium.

8. A method according to claim 1, wherein the amount of resazurin present in the mixture is 7.5–50 mg per liter of medium.

* * * * *